US012417961B2

(12) United States Patent
Fan et al.

(10) Patent No.: US 12,417,961 B2
(45) Date of Patent: Sep. 16, 2025

(54) CHIP HEAT SINK AND NUCLEIC ACID EXTRACTION DEVICE

(71) Applicants: Beijing BOE Technology Development Co., Ltd., Beijing (CN); BOE TECHNOLOGY GROUP CO., LTD., Beijing (CN)

(72) Inventors: Beiyuan Fan, Beijing (CN); Ding Ding, Beijing (CN)

(73) Assignees: Beijing BOE Technology Development Co., Ltd., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 18/016,411

(22) PCT Filed: Jan. 28, 2022

(86) PCT No.: PCT/CN2022/074515
§ 371 (c)(1),
(2) Date: Jan. 16, 2023

(87) PCT Pub. No.: WO2023/141916
PCT Pub. Date: Aug. 3, 2023

(65) Prior Publication Data
US 2024/0249997 A1 Jul. 25, 2024

(51) Int. Cl.
H01L 23/00 (2006.01)
B01L 3/00 (2006.01)
H01L 23/46 (2006.01)

(52) U.S. Cl.
CPC ........ H01L 23/46 (2013.01); B01L 3/502761 (2013.01); B01L 2300/1811 (2013.01); B01L 2300/1838 (2013.01)

(58) Field of Classification Search
CPC ..... H01L 23/46; H01L 23/476; H01L 23/367; H01L 23/3672; H01L 23/3677
See application file for complete search history.

(56) References Cited

U.S. PATENT DOCUMENTS

2010/0112667 A1  5/2010  Sundaram et al.
2014/0186936 A1  7/2014  Tanaka et al.
(Continued)

FOREIGN PATENT DOCUMENTS

CN    105015200 A    11/2015
CN    205687904 U    11/2016
(Continued)

OTHER PUBLICATIONS

WIPO, International Search Report issued on Jun. 23, 2021 for application No. PCT/CN2020/116853.
(Continued)

Primary Examiner — Reema Patel
(74) Attorney, Agent, or Firm — HOUTTEMAN LAW LLC

(57) ABSTRACT

A chip heat sink for a chip and a nucleic acid extraction device, where the chip has a channel for conveying a fluid, and on/off of the channel is controlled by an solenoid valve, the chip heat sink includes: a substrate, where the substrate has a first surface for placing the chip, and the first surface is provided with a first accommodating groove for accommodating an electromagnet; and a heat dissipation structure on the substrate and for dissipating heat from the electromagnet.

20 Claims, 6 Drawing Sheets

(56) References Cited

U.S. PATENT DOCUMENTS

2015/0361419 A1    12/2015   Kim et al.
2017/0292146 A1    10/2017   Singer et al.

FOREIGN PATENT DOCUMENTS

| | | |
|---|---|---|
| CN | 108841818 A | 11/2018 |
| CN | 109536366 A | 3/2019 |
| CN | 110257245 A | 9/2019 |
| CN | 110343611 A | 10/2019 |
| CN | 111378573 A | 7/2020 |
| CN | 111592971 A | 8/2020 |
| CN | 212426057 U | 1/2021 |
| CN | 112322453 A | 2/2021 |
| CN | 214946820 U | 11/2021 |
| JP | 2005253365 A | 9/2005 |
| JP | 2013183081 A | 9/2013 |

OTHER PUBLICATIONS

WIPO, International Search Report issued on Oct. 26, 2022 for application No. PCT/CN2022/108153.

though the electromagnet is not powered on, the fluid can still pass through the position of the solenoid valve.

CHIP HEAT SINK AND NUCLEIC ACID EXTRACTION DEVICE

TECHNICAL FIELD

The present disclosure relates to the technical field of chip heat dissipation, and particularly to a chip heat sink and a nucleic acid extraction device.

BACKGROUND

Point-of-care testing (POCT) refers to clinical testing and bedside testing performed beside a patient, this testing method is not always performed by a clinical tester, but an analysis is performed immediately at a sampling site, so that a complicated processing procedure of a sample during laboratory testing is omitted, and the method is a new method for rapidly obtaining a testing result. The POCT instrument has the characteristics of rapidness, simplicity and comprehensive cost saving. For example, a nucleic acid extractor can extract nucleic acids from a biological sample, which is a necessary sample processing procedure for subsequent nucleic acid detection.

For a chip-type POCT nucleic acid extractor, a microfluidic chip is generally used for extracting nucleic acid, an solenoid valve is further required to control the on/off of a fluid channel in the chip. When a fluid is required to flow through the position of the solenoid valve, the electromagnet may be controlled to be powered off, and the fluid can pass through the position of the solenoid valve without obstruction. When the fluid is required to not flow through the position of the solenoid valve, the electromagnet may be controlled to be powered on forward, and the fluid is blocked and unable to flow through the position of the electromagnet.

However, the electromagnet generates heat when being powered on due to the joule heat effect. According to the result of an experiment, the electromagnet generates heat for a certain period of time and reaches 90° C. or above. Too high temperature of the electromagnet not only affects the effect of nucleic acid extraction, but also damages instruments and chips.

SUMMARY

The present disclosure aims to solve at least one technical problem in the prior art and provides a chip heat sink and a nucleic acid extraction device, which can solve the problem of heat generation of an electromagnet.

In order to achieve the above object, the present disclosure provides a chip heat sink for a chip, where the chip has a channel for conveying a fluid, and on/off of the channel is controlled by a solenoid valve, and the chip heat sink includes:
  a substrate, where the substrate has a first surface for placing the chip, and the first surface is provided with a first accommodating groove for accommodating an electromagnet; and
  a heat dissipation structure on the substrate and for dissipating heat from the electromagnet.

Alternatively, a shape of an orthographic projection of the first accommodating groove on the first surface is the same as a shape of an orthographic projection of the electromagnet on the first surface.

Alternatively, a space exists between an outer surface of the electromagnet and an inner surface of the first accommodating groove opposite to the outer surface, and a thermally conductive material is filled in the space.

Alternatively, a part of the electromagnet protrudes with respect to the first surface.

Alternatively, the first surface is further provided with a lead recessed channel and a connecting groove connected between a first end of the lead recessed channel and the first accommodating groove, where the lead recessed channel is used for accommodating a power supply lead of the electromagnet, and a second end of the lead recessed channel extends to an edge of the substrate; and
  the connecting groove is used for accommodating a connecting part between the electromagnet and the power supply lead.

Alternatively, a number of the first accommodating groove is one or more, and a number of the connecting groove is the same as the number of the first accommodating groove, and the one or more connecting grooves are connected to the one or more accommodating grooves in a one-to-one correspondence;
  a number of the lead recessed channel is the same as the number of the first accommodating groove, and first ends of the lead recessed channels are connected to the connecting grooves in a one-to-one correspondence; second ends of the lead recessed channels independently extend to a same edge of the substrate; or
  the first surface is further provided with a main lead recessed channel, one end of the main lead recessed channel extends to an edge of the substrate, at least one of the second ends of all the lead recessed channels is connected to the main lead recessed channel, and the second ends of the lead recessed channels not connected to the main lead recessed channel independently extend to the edge of the substrate where the one end of the main lead recessed channel is located; or
  the first surface is further provided with a branch lead recessed channel and a main lead recessed channel, one end of the main lead recessed channel extends to an edge of the substrate, the branch lead recessed channel includes at least one branch lead recessed channel, a first end of each of the at least one branch lead recessed channel is connected to a second end of at least two of the lead recessed channels, and a second end of the branch lead recessed channel is connected to the main lead recessed channel; the second end of the lead recessed channel not connected to the branch lead recessed channel is connected to the main lead recessed channel or independently extends to the edge of the substrate where the one end of the main lead recessed channel is located.

Alternatively, the chip further includes at least one syringe, and the first surface is further provided with at least one second accommodating groove each for accommodating a part of one of the at least one syringe, and a number and a position of the at least one second accommodating groove is in one-to-one correspondence with a number and a position of the at least one syringe.

Alternatively, the first surface is further provided with at least one positioning slot, and a number, a shape and a position of the at least one positioning slot are adapted to a number, a shape and a position of at least one designated protrusions on an outer surface of the chip, so that the at least one positioning slot is matched with the at least one designated protrusion to define a position of the chip on the first surface.

Alternatively, two edge protrusions are further provided at two edges of the first surface on two opposite sides and protrude relative to the first surface, and surfaces of the two edge protrusions opposite to each other and the first surface form an accommodating space for defining the chip.

Alternatively, the heat dissipation structure includes:
a plurality of fins arranged at intervals on a second surface of the substrate away from the first surface; and
a fan arranged on a side of the plurality of fins away from the substrate and for blowing air to the plurality of fins in a direction toward the second surface.

Alternatively, the fan is attached and fixedly connected to the plurality of fins.

Alternatively, the chip heat sink further includes a support, where the support is on a side of the substrate away from the first surface, one end of the support is fixedly connected to the substrate, and the other end of the support is used to be fixedly connected to a nucleic acid extraction device where the chip is located.

Alternatively, the heat dissipation structure includes:
an annular cooling component around the electromagnet along an inner peripheral wall of the first accommodating groove, where the annular cooling component includes an annular body having a cooling channel and a circulation pump communicated with two ends of the cooling channel, and the cooling channel is used for conveying a cooling medium; and the circulation pump is used for circulating the cooling medium in the cooling channel.

Alternatively, the annular body includes a cooling pipe wound in a cylindrical spiral configuration.

Alternatively, the heat dissipation structure includes:
a cooling channel formed in the substrate for conveying a cooling medium, where the cooling channel includes a cooling section in a shape of a flat plate and two lead-out sections, where the cooling section is on a side of a bottom surface of the first accommodating groove away from the first surface; the two lead-out sections are connected to two ends of the cooling section, respectively, and the other end of each of the two lead-out sections extends to an outer surface of the substrate; and
a circulation pump, where an output end and an input end of the circulation pump are connected to the other ends of the two lead-out sections, respectively, for circulating the cooling medium in the cooling channel.

Alternatively, the cooling section is wound in a planar spiral configuration.

Alternatively, the chip is a nucleic acid extraction microfluidic chip.

As another technical solution, an embodiment of the present disclosure further provides a nucleic acid extraction device, including a nucleic acid extraction microfluidic chip and the chip heat sink provided in the embodiment of the present disclosure, where the nucleic acid extraction microfluidic chip is on the first surface of the substrate in the chip heat sink.

The present disclosure has the following beneficial effects:

The chip heat sink provided by the embodiment of the present disclosure includes a substrate and a heat dissipation structure, where the substrate has a first surface for placing a chip, and the first surface is provided with a first accommodating groove for accommodating an electromagnet; the heat dissipation structure is arranged on the substrate and used for dissipating heat from the electromagnet. Therefore, it can not only avoid the too high temperature of electromagnet affecting the effect of nucleic acid extraction and damaging the equipment and chip, but also indirectly control the temperature of the chip by controlling the temperature of the substrate through the heat dissipation structure, so as to enable the temperature of the chip to reach the operating temperature of an reaction such as loop-mediated isothermal amplification, polymerase chain reaction, or the like.

In the nucleic acid extraction device provided by the embodiment of the present disclosure, by adopting the chip heat sink provided by the embodiment of the present disclosure, it can not only avoid the too high temperature of electromagnet affecting the effect of nucleic acid extraction and damaging the equipment and chip, but also indirectly control the temperature of the chip by controlling the temperature of the substrate through the heat dissipation structure, so as to enable the temperature of the chip to reach the operating temperature of an reaction such as loop-mediated isothermal amplification, polymerase chain reaction, or the like.

DETAIL DESCRIPTION OF EMBODIMENTS

Figure 1:
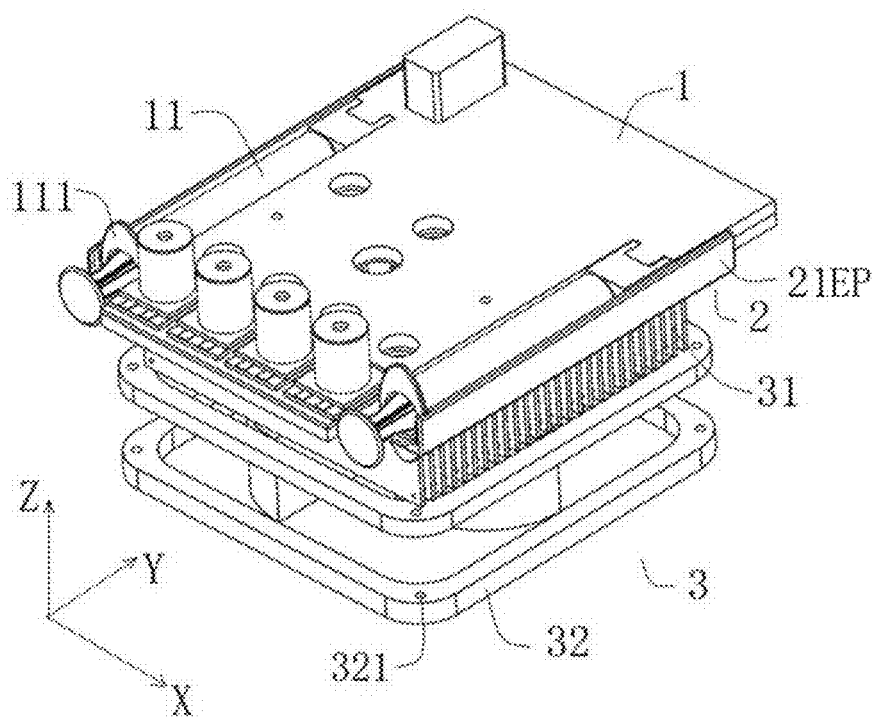
FIG. 1 is a diagram illustrating a structure of a chip heat sink when a chip is placed thereon provided by a first embodiment of the present disclosure.

In order to enable one of ordinary skill in the art to better understand the technical solutions of the present disclosure, a chip heat sink and a nucleic acid extraction device provided by the present disclosure will be described in detail below with reference to the accompanying drawings.

First Embodiment

The embodiment of the present disclosure provides a chip heat sink, which has a channel for conveying fluid, and the on/off of the channel is controlled by a solenoid valve. Taking the chip being a nucleic acid extraction microfluidic chip as an example, a plurality of liquid flow channels are arranged on a channel plate layer of the chip, and each of the channels is provided a solenoid valve. The solenoid valve includes a spool and an elastic membrane. When an electromagnet is powered off, the spool and the elastic membrane are not subjected to external magnetic force and are in an initial state, in this case, the channel is in a conduction state, so that the normal flow of liquid is ensured. When the electromagnet is powered on, the electromagnet adsorbs the spool to shift, the elastic membrane generates deformation under the pressure action of the spool, and in this case, the channel is in a cut-off state, so that the liquid flow is blocked. In practical applications, the solenoid valves with other structures may alternatively be adopted, which are not particularly limited by the embodiments of the present disclosure. In addition, the electromagnet may be a structure independent from the nucleic acid extraction microfluidic chip.

Based on the joule heat effect, the electromagnet generates heat when being powered on, and according to an experimental result, the electromagnet generates heat for a certain time and then reaches more than 90° C. Too high temperature of the electromagnet not only affects the effect of nucleic acid extraction, but also damages instruments and chips. Therefore, referring to FIGS. 1 to 3 together, the present embodiment provides a chip heat sink, including a substrate 2 and a heat dissipation structure 3. The substrate 2 has a first surface 2a for placing the chip 1, a first accommodating groove 21 is formed on the first surface 2a, and the first accommodating groove 21 is used for accommodating an electromagnet 4. The heat dissipation structure 3 is disposed on the substrate 2, and is used for dissipating heat generated by the electromagnet 4.

Through placing electromagnet 4 in the first accommodating groove 21, the heat generated by the electromagnet 4 may be exported through the substrate 2, and be dissipated out by the heat radiation structure 3, so that the electromagnet 4 may be effectively cooled off, to avoid the high temperature of electromagnet 4 affecting the effect of nucleic acid extraction and damaging the equipment and chip. In addition, the heat dissipation structure 3 may be used to control the temperature of the substrate 2 to indirectly control the temperature of the chip 1, so that the temperature of the chip 1 may reach an operating temperature of a reaction such as a polymerase chain reaction (PCR), a loop-mediated isothermal amplification (loop-mediated isothermal amplification, LAMP), or the like.

Specifically, the operating temperature of the polymerase chain reaction (PCR) varies as follows: in a pre-denaturation stage, the operating temperature is controlled at 95° ° C. for 5 minutes; in a temperature rising and falling stage, a temperature rising step and a temperature falling step are executed alternately for 40 times, the operating temperature is raised to 95° C. and maintained for 25 s (i.e., 25 seconds) in the temperature rising step; and the operating temperature is reduced to 55° C. and maintained for 35 s in the temperature falling step; and in an extension stage, the operating temperature is controlled at 72° C. for 1 minute. The loop-mediated isothermal amplification (LAMP) requires that the operating temperature is controlled to be about 63° C. and the temperature is kept for 30 to 60 minutes. In the reaction process described above, the temperature of the substrate 2 may be controlled through the heat dissipation structure 3, so that the temperature of the chip 1 may be controlled to reach the corresponding operating temperature, and the normal running of a polymerase chain reaction (PCR) or a loop-mediated isothermal amplification (LAMP) can be ensured.

Figure 5:
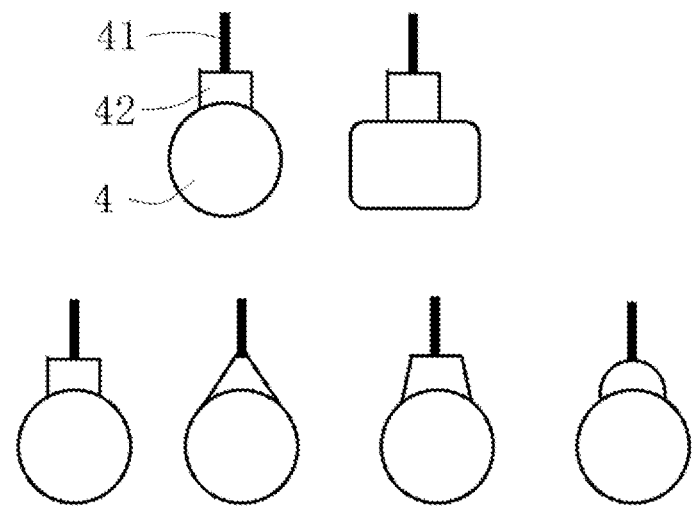
FIG. 5 is a schematic view of a plurality of connecting grooves with different shapes adopted in the first embodiment of the present disclosure.

In some alternative embodiments, a shape of an orthographic projection of the first accommodating groove 21 on the first surface 2a is the same as a shape of an orthographic projection of the electromagnet 4 on the first surface 2a. By the arrangement, the effect of heat dissipation of the electromagnet 4 can be ensured, and the uniformity of heat dissipation can be improved. In practical applications, orthographic projections of different types of electromagnets 4 on the first surface 2a may have different shapes, such as a circle (as shown in FIG. 5), a rectangle (as shown in FIG. 5), a square, and so on.

Figure 3:
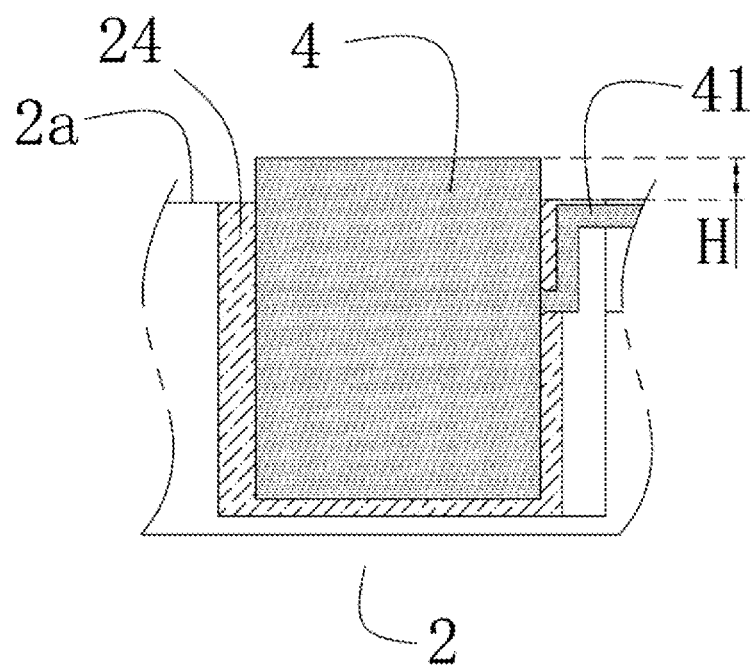
FIG. 3 is a cross-sectional view of one of the first accommodating grooves and an electromagnet adopted in the first embodiment of the present disclosure.

In some alternative embodiments, the electromagnet 4 may be embedded in the first accommodating groove 21. That is, an outer surface of the electromagnet 4 is attached to an inner surface of the first accommodating groove 21, so as to ensure the effect of heat dissipation, but this is not beneficial to the installation and uninstallation of the electromagnet 4. For this reason, in some alternative embodiments, a space may be provided between the outer surface (including an outer peripheral surface and a bottom surface) of the electromagnet 4 and the inner surface (including a side surface and a bottom surface) of the first accommodating groove 21 opposite to the outer surface of the electromagnet 4. For example, if the shapes of the orthographic projections of the electromagnet 4 and the first accommodating groove 21 on the first surface 2a are both circular, a diameter of the first accommodating groove 21 is greater than that of the electromagnet 4. In this case, in order to improve the effect of heat dissipation, as shown in FIG. 3, the above described space is filled with a thermally conductive material 24 for conducting the heat generated by the electromagnet 4 to the substrate 2. The thermally conductive material 24 may be a non-magnetic material with good thermal conductivity, such as thermally conductive silicone grease. Alternatively, the diameter of the first accommodating groove 21 is greater than the diameter of the electromagnet 4 by 0.5 mm to 1 mm.

In some alternative embodiments, as shown in FIG. 3, a part of the electromagnet 4 protrudes with respect to the first surface 2a by a height H, which is set to facilitate the electromagnet 4 to attract the spool in the solenoid valve without interference from the substrate 2. The height H of the protruding part should be designed to maximize a contact area between the electromagnet 4 and the substrate 2, so as to ensure the effect of heat dissipation. The height H is, for example, in a range of 1 mm to 2 mm. Taking the shapes of orthographic projections of the electromagnet 4 and the first accommodating groove 21 on the first surface 2a being both circular as an example, if the diameter and the height of the electromagnet 4 are 12 mm×12 mm, then the diameter and the depth of the first accommodating groove 21 may be 12.5 mm×11 mm.

Figure 2:
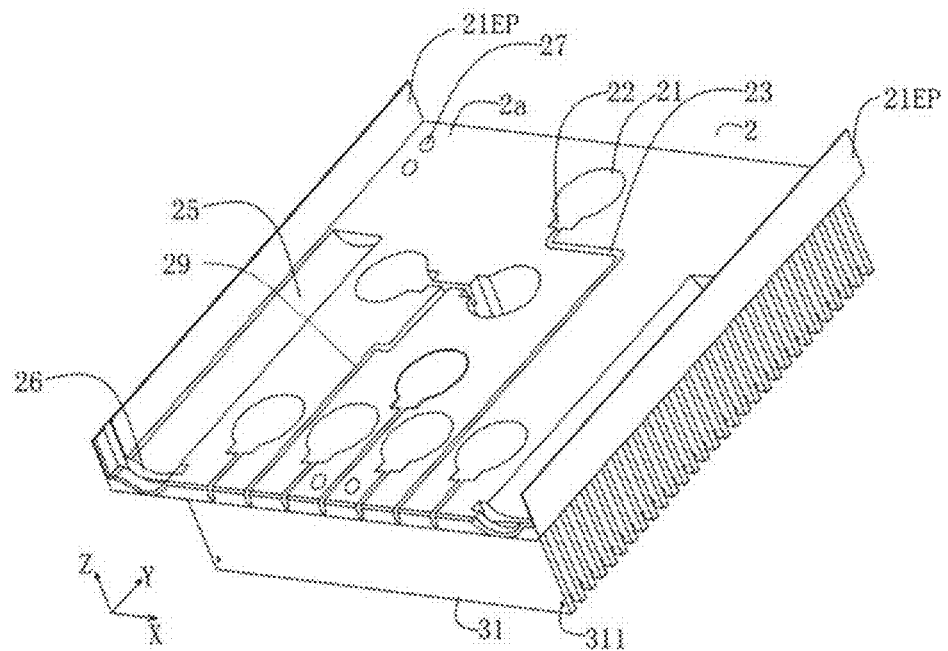
FIG. 2 is a diagram illustrating a structure of the chip heat sink when no chip is placed thereon provided by the first embodiment of the present disclosure.
Figure 4:
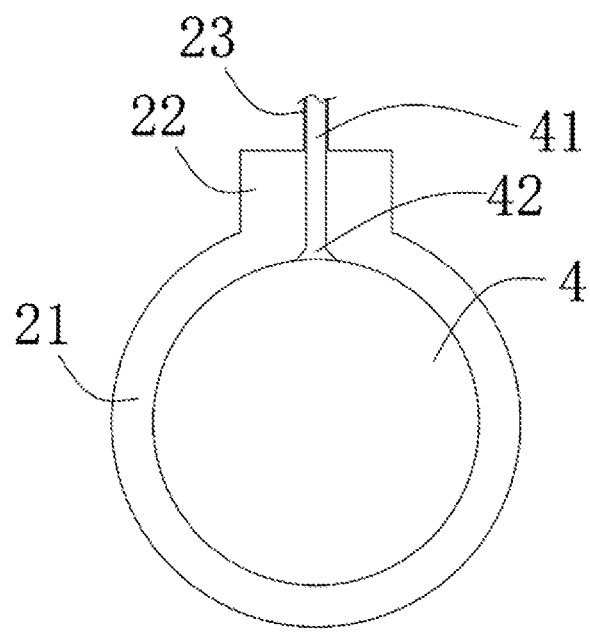
FIG. 4 is a top view of one of the first accommodating grooves and the electromagnet provided by the first embodiment of the present disclosure.

In some alternative embodiments, as shown in FIGS. 2 to 4, the first surface 2a is further provided with a lead recessed channel 23 and a connecting groove 22 connected between a first end (i.e., an end close to the first accommodating groove 21) of the lead recessed channel 23 and the first accommodating groove 21. The lead recessed channel 23 is used for accommodating a power supply lead 41 of the electromagnet 4, and a second end (i.e., an end away from the first accommodating groove 21) of the lead recessed channel 23 extends to an edge of the substrate 2. With an aid of the lead recessed channel 23, It can not only accommodate the power supply lead 41, ensuring that the chip 1 can be attached to the first surface 2a when the chip 1 is installed on the first surface 2a, but also lead the power supply lead 41 to the edge of the substrate 2, so that the power supply lead 41 can be connected to an external power supply. Alternatively, a depth of the lead recessed channel 23 is greater than or equal to 2 mm.

The connecting groove 22 is used for accommodating a connecting part 42 between the electromagnet 4 and the power supply lead 41, and the connecting part 42 is usually coated with fixing glue. In order to improve the effect of heat dissipation of the connecting part 42, Alternatively, a shape of an orthographic projection of the connecting groove 22 on the first surface 2a is substantially the same as a shape of an orthographic projection of the connecting part 42 on the first surface 2a (i.e., a shape of an orthographic projection of a contour of the fixing glue on the first surface 2a). For example, as shown in FIG. 5, the shape of the orthographic projection of the connecting part 42 on the first surface 2a includes a rectangle, a square, a triangle, a trapezoid, a semicircle, or the like. In practical applications, one of the above shapes may be selected according to the processing difficulty, where the trapezoid (preferably an isosceles trapezoid) is closest to the shape of the current connecting part 42, and has the best effect of thermal conduction. Further, since the circle has no dead space, it can be adapted to more various shapes of the connecting part 42.

In some alternative embodiments, the number of the first accommodating grooves 21 is one or more. For example, FIGS. 2 and 6 each show eight first accommodating grooves 21, but the embodiments of the present disclosure are not limited thereto. In practical applications, the number and positions of the first accommodating grooves 21 may be adaptively changed according to the number and positions of the electromagnets. The number of the connecting grooves 22 is the same as the number of the first accommodating grooves 21, and the connecting grooves 22 are connected to the first accommodating grooves 21 in a one-to-one correspondence.

The number of the lead recessed channels 23 is the same as the number of the first accommodating grooves 21, and the first ends of the first accommodating grooves 21 are connected to the connecting grooves 22 in a one-to-one correspondence. In a specific embodiment, as shown in FIG. 2, in second ends of eight lead recessed channels 23, the second ends of six lead recessed channels 23 independently extend to the edge of the substrate 2 on the same side. For example, the second ends of the six lead recessed channels 23 extend to the same edge of the substrate 2 parallel to an X direction and away from the first accommodating groove 21. The second ends of the remaining two lead recessed channels 23 are connected to a main lead recessed channel 29 formed on the first surface 2a. One end of the main lead recessed channel 29 extends to the same edge where the second ends of the six lead recessed channels 23 are located. Thus, the second ends of all the lead recessed channels 23 are located at the same edge, and all the power supply leads 41 are led out from the same edge of the substrate 2, so that a convenience is provided for connection to the external power supply, processing steps can be reduced, and the design of the heat dissipation structure 3 with a smaller volume is facilitated under a condition that the effect of heat dissipation is guaranteed.

Figure 6:
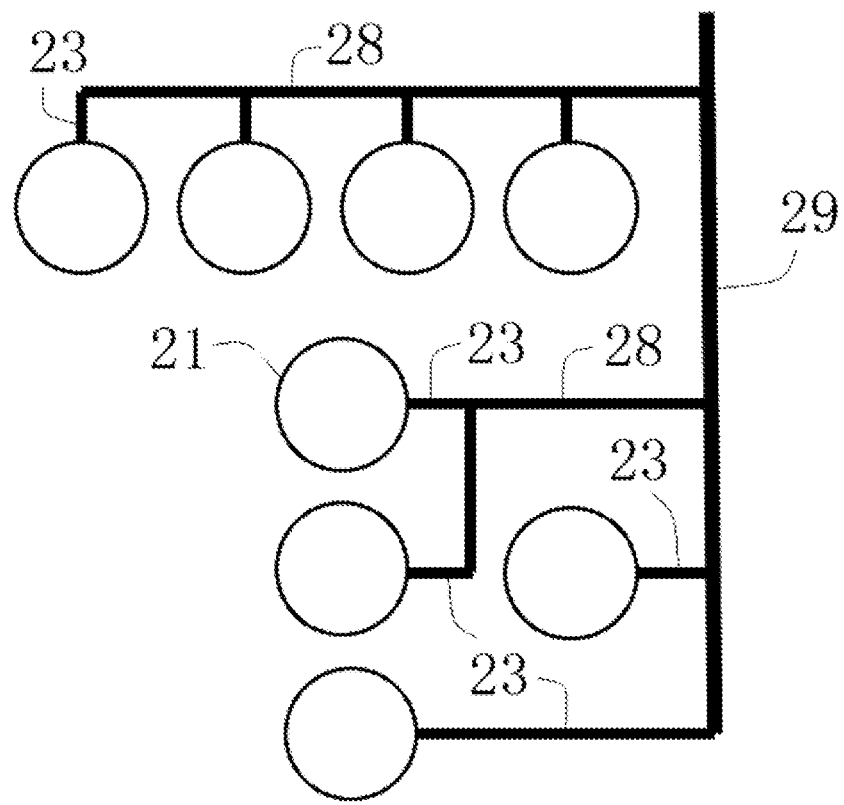
FIG. 6 is a schematic diagram of traces of a lead recessed channel, a branch lead recessed channel and a main lead recessed channel provided by the first embodiment of the present disclosure.

In another specific embodiment, as shown in FIG. 6, in the second ends of the eight lead recessed channels 23, the second ends of four lead recessed channels 23 are connected to one of branch lead recessed channels 28 formed on the first surface 2a, and one end of this branch lead recessed channel 28 is connected to the main lead recessed channel 29. The second ends of other two lead recessed channels 23 are connected to another branch lead recessed channel 28, and one end of this branch lead recessed channel 28 is also connected to the main lead recessed channel 29. The second ends of the remaining two lead recessed channels 23 are directly connected to the main lead recessed channel 29, and one end of the main lead recessed channel 29 extends to an edge of the substrate 2 on a side thereof. Thus, it is also achieved that the second ends of all the lead recessed channels 23 are located at the same edge.

The embodiment of the present disclosure is not limited to the above described layout of the lead recessed channels 23. In practical applications, a suitable layout may be selected according to specific requirements. That is, one manner or a combination of a plurality of different manners may be selected from three lead-out manners (independently extending to the same edge of the substrate 2, directly connecting to the main lead recessed channel 29, and indirectly connecting to the main lead recessed channel 29 through the branch lead recessed channel 28) of the second end of the lead recessed channel 23.

In some alternative embodiments, as shown in FIG. 1, the chip 1 further has at least one syringe 11, for example two syringes 11 as shown in FIG. 1, both of which are needle syringes. In this case, as shown in FIG. 2, the first surface 2a is further provided with a second accommodating groove 25 for accommodating a part of the syringe 11. The number and positions of the second accommodating grooves 25 are set in one-to-one correspondence with the number and positions of the syringes 11. For example, in order to place the two syringes 11 shown in FIG. 1, two second accommodating grooves 25 are provided and are correspondingly arranged at edges of the first surface 2a on both side in the X direction. Alternatively, an inner surface of the second accommodating groove 25 is shaped to adapt to an outer surface of the syringe 11. In addition, for a needle syringe, as shown in FIG. 1, one end of the second accommodating groove 25 extends to one edge of the substrate 2, and the length of the second accommodating groove 25 in a Y direction is adapted to the length of a barrel of the needle syringe, and a plunger of the needle syringe may protrude from the edge of the substrate 2, so that the plunger will not be interfered by the substrate 2 when the plunger moves telescopically in the barrel.

In some alternative embodiments, as shown in FIG. 2, the first surface 2a is further provided with at least one positioning slot 26, and the number, shapes and positions of the positioning slots 26 are adapted to the number, shapes and positions of the designated protrusions on an outer surface of the chip 1, so that the positioning slots 26 cooperate with the designated protrusions to define the position of the chip 1 on the first surface 2a. In practical applications, the above described designated protrusions may be protrusions formed on any component in the chip 1, or protrusions specially provided on the chip 1 for positioning. For example, for a needle syringe, as shown in FIG. 1, a part of the positioning slot 26 is located in the second accommodating groove 25, and the depth of the positioning slot 26 is greater than the depth of the second accommodating groove 25. The designated protrusion on the outer surface of the syringe 11 is a flange at an edge of the barrel of the needle syringe, and the flange may be matched with the positioning slot 26, so that the position of the syringe 11 on the first surface 2a can be defined, and the barrel of the needle syringe can be ensured to be attached to the inner surface of the second accommodating groove 25.

In some alternative embodiments, as shown in FIG. 2, two edge protrusions 21EP protruding relative to the first surface 2a are further disposed at two edges of the first surface 2a on two opposite sides, respectively. For example, the two edge protrusions 21EP are oppositely disposed at two edges of the substrate 2 parallel to the Y direction and protrude in the Z direction relative to the first surface 2a. Thus, as shown in FIG. 1, the surfaces of the two edge protrusions 21EP opposite to each other and the first surface 2a form an accommodating space for defining the chip 1, thereby serving to fix the chip 1.

Taking the two syringes 11 shown in FIG. 1 as an example, two second accommodating grooves 25 are provided, and are located at positions close to the two edge protrusions 21EP, respectively. In this case, in order to further stably fix the syringes 11, Alternatively, as shown in FIG. 2, a part of the positioning slot 26 is formed on the first surface 2a, and another part is formed on a surface of one of the edge protrusions 21EP opposite to the other edge protrusion 21EP. That is, each edge protrusion 21EP also has a groove capable of accommodating a part of the above described designated protrusion.

Figure 7:
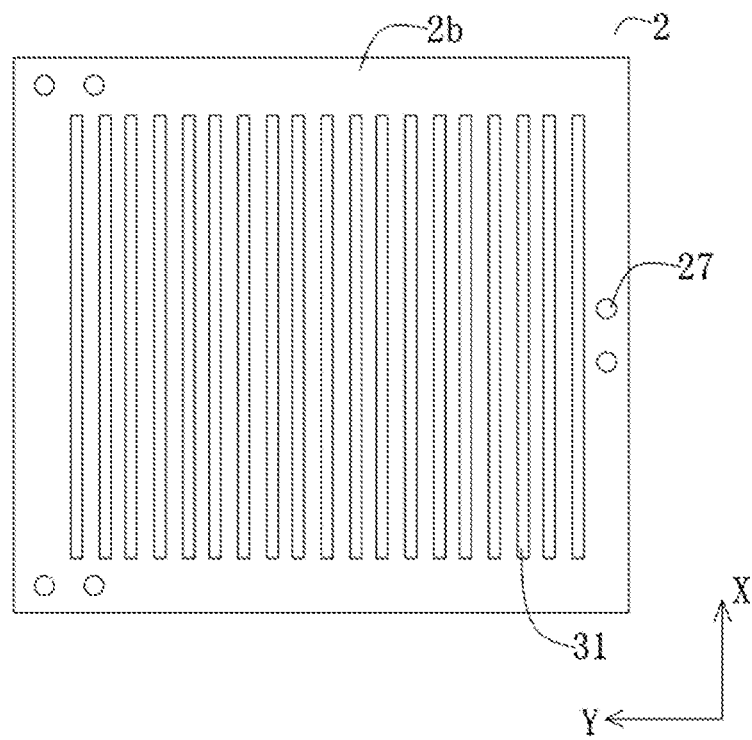
FIG. 7 is a diagram illustrating a structure of a side of the chip heat sink away from the chip provided by the first embodiment of the present disclosure.

In some alternative embodiments, as shown in FIG. 1, the heat dissipation structure 3 includes a plurality of fins 31 and a fan 32, where the fins 31 may be made of a non-magnetic thermally conductive material with good thermal conductivity, preferably aluminum. As shown in FIG. 7, a plurality of fins 31 are arranged at intervals on a second surface 2b of the substrate 2 away from the first surface 2a. Alternatively, the plurality of fins 31 are parallel to each other and perpendicular to the second surface 2b. In one specific embodiment, the plurality of fins 31 are arranged in a row at equal intervals along the Y direction, and a length direction of each fin 31 is parallel to the X direction, so that the fins may be uniformly arranged on the second surface 2b, and thus uniform heat dissipation may be achieved for the substrate 2a.

In one specific embodiment, the fins 31 have a thickness of 1 mm in the Y direction, a length of 78 mm in the X direction, a width of 19 mm in the Z direction, and a spacing of 2 mm between two adjacent fins 31. However, the embodiment of the present disclosure is not limited thereto, and in practical applications, the number, size, and layout of the fins 31 may be adaptively designed by comprehensively considering the material processing conditions of the fins 31, the size of the chips 1, and the size of the fans 32, which are not particularly limited by the embodiment of the present disclosure.

Figure 8:
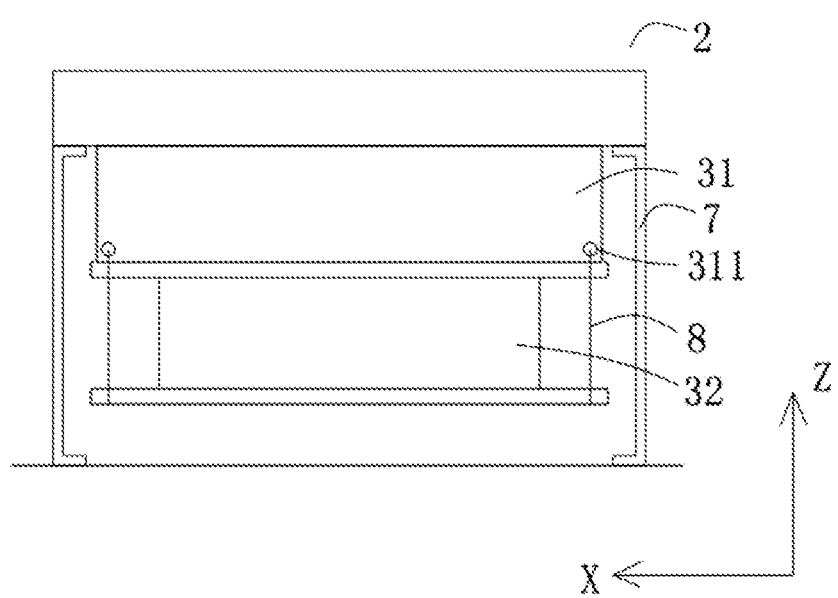
FIG. 8 is a schematic diagram illustrating how to mount the chip heat sink provided by the first embodiment of the present disclosure.

As shown in FIGS. 1 and 8, the fan 32 is disposed on a side of the plurality of fins 31 away from the substrate 2, and is used for blowing air to the plurality of fins 31 in a direction toward the second surface 2b, so as to accelerate dissipating heat from the substrate 2 by the fins 31, and indirectly dissipate heat from the electromagnet 4 and components in the chip 1. In one specific embodiment, the fan 32 may adopt a fan having a length, a width, and a height of 80 mm×80 mm×25 mm, and a direct current voltage of 24V.

In some alternative embodiments, the fan 32 is attached to and fixedly connected to the plurality of fins 31, so as to improve the heat dissipation efficiency of the fan 32. In addition, the fan 32 may be fixedly connected to the fins 31 in various manners. For example, as shown in FIGS. 2 and 8, a plurality of first through holes 311 penetrating through the fins 31 in the Y direction are correspondingly provided in the plurality of fins 31, a plurality of second through holes 321 (for example, provided at four corners of the fan 32) are correspondingly provided in the fan 32, the fixing strings 8 are passed through the first through holes 311 in all the fins 31, then passed through the corresponding second through holes 321 in the fan 32, and the fan 32 and all the fins 31 are bound by knotting the fixing strings 8. The manner in which the fixing strings 8 are passed through the first through holes 311 and the second through holes 321 may be freely set, as long as the fan 32 and all the fins 31 can be bound together. Alternatively, in practical applications, the fan 32 and the pins 31 may be fixedly connected together by other means, such as adhesion.

In some alternative embodiments, the fan 32 may be connected to a controller (not shown) for controlling the on/off of the fan 32 by controlling the power on or off. Specifically, the controller may control the temperature of the substrate 2 by controlling the on/off of the fan 32, thereby indirectly controlling the chip temperature so that the chip temperature satisfies an operating temperature, such as an operating temperature of the loop-mediated isothermal amplification.

It was found through experiments that the temperature of the electromagnet reached 125° C. till the chip without the heat sink was used to the $2^{nd}$ minute, while the temperatures of the electromagnet and the substrate corresponding to the $1^{st}$ minute to the $8^{th}$ minute of operation of the chip with the heat sink disclosed in this embodiment were as shown in table 1 below.

TABLE 1

| Time (min) | 0 | 1 | 2 | 3 | 4 | 5 | 6 | 7 | 8 |
|---|---|---|---|---|---|---|---|---|---|
| Electromagnet temperature (° C.) | 23 | 46 | 50 | 52 | 52 | 52 | 53 | 52 | 52 |
| Substrate temperature (° C.) | 23 | 28 | 30 | 31 | 31 | 32 | 32 | 32 | 32 |

As can be seen from Table 1, the temperature of the electromagnet does not exceed 53° C. and the temperature of the substrate is maintained at 32° C. during the time period from the $1^{st}$ minute to the $8^{th}$ minute of operation of the chip. It can be seen that, the temperature of the electromagnet is effectively controlled, the effect of nucleic acid extraction is not affected, and the device and the chip are not damaged. Meanwhile, the temperature of the substrate is maintained at 32° C., so that not only the operation of the chip is not affected, but also the requirement on the operating temperature of the chip can be met.

In some alternative embodiments, as shown in FIG. 8, the chip heat sink further includes a support 7, which is located on a side of the substrate 2 away from the first surface 2a. One end of the support 7 is fixedly connected to the substrate 2, and the other end is used for fixedly connecting to a nucleic acid extraction device on which the chip 1 is located, for example, is fixed on the housing or other component of the nucleic acid extraction device. The above described support 7 can not only serve to support and fix the substrate 2, but also form a space for accommodating the pins 31 and the fan 32 between the substrate 2 and an installation surface of the nucleic acid extraction device.

Specifically, as shown in FIG. 7, a plurality of mounting holes 27 are provided in the substrate 2, and penetrate though the substrate 2 in the Z direction. In one specific embodiment, the plurality of mounting holes 27 are divided into three groups, which are respectively located at three edges of the substrate 2, and each group has two mounting holes 27. Correspondingly, the above described support 7 is composed of three support legs, and the two mounting holes 27 in each group are screwed with one end of one support leg by two screws, and the other end of the support leg is screwed with the nucleic acid extraction device on which the chip 1 is located by a plurality of (e.g., three) screws.

Second Embodiment

Figure 9:
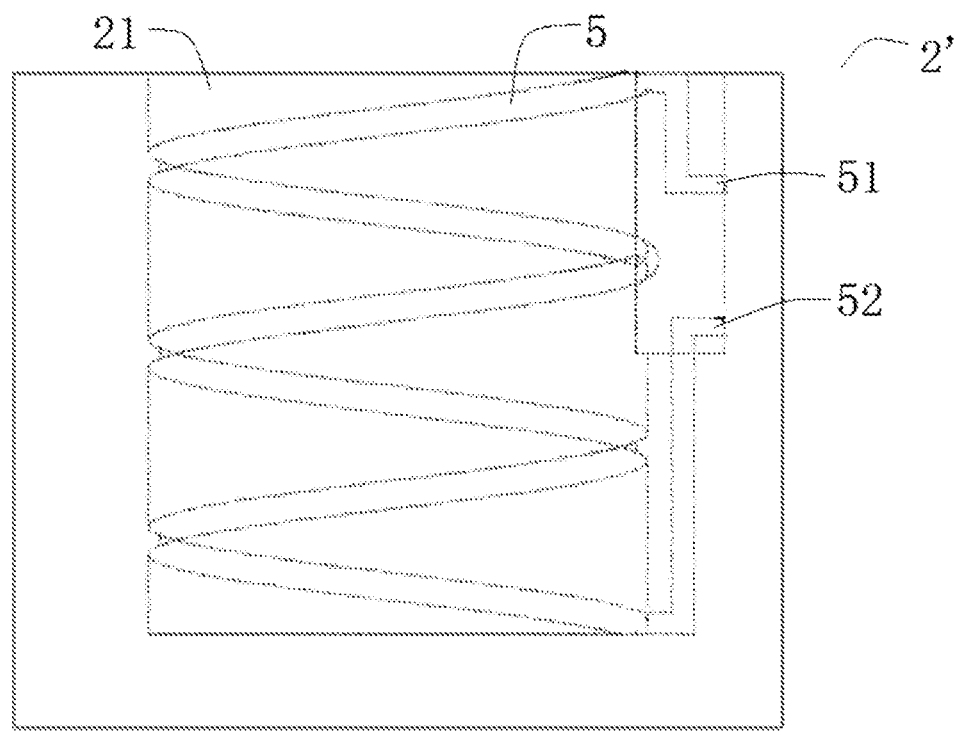
FIG. 9 is a diagram of seeing through a heat dissipation structure in one of the first accommodating grooves adopted in a second embodiment of the present disclosure.

Compared with the first embodiment, a chip heat sink provided by the present embodiment has a different heat dissipation manner from that of the first embodiment. Specifically, as shown in FIG. 9, in the present embodiment, the heat dissipation structure includes an annular cooling component 5, and the annular cooling component 5 is disposed around the electromagnet (not shown in the drawings) along the inner peripheral wall of the first accommodating groove 21 in the substrate 2'. Specifically, a space may be provided between the inner peripheral surface of the first accommodating groove 21 and the outer peripheral surface of the electromagnet, and the annular cooling component 5 is disposed around in the space. The annular cooling component 5 may be in contact with the outer peripheral surface of the electromagnet, or a thermally conductive material may be filled between the annular cooling component 5 and the outer peripheral surface of the electromagnet.

Moreover, the annular cooling module 5 includes an annular body having a cooling channel and a circulation pump (not shown in the drawings) communicated with both ends of the cooling channel. The cooling channel is used for conveying a cooling medium (e.g., cooling water), and the circulation pump is used for circulating the cooling medium in the cooling channel. Specifically, an output end and an input end of circulation pump are connected to an input end and an output end (51, 52) of the cooling channel, respectively. The circulation pump puts cooled water into the cooling channel through output end, the cooling water may carry out a heat exchange with the electromagnet during flowing through the cooling channel, takes away the heat generated by the electromagnet, then flows back in the circulation pump through the input end of the circulation pump to be cooled off again. The annular body is preferably made of a material which has a good heat resistance and is easy to process.

In some alternative embodiments, the annular body includes a cooling pipe wound in a cylindrical spiral configuration, and an internal channel of the cooling pipe is the cooling channel. In practical applications, the cooling pipe may alternatively adopt other winding manners, such as a serpentine winding manner or the like.

The cooling pipe may be disposed inside the inner circumferential surface of the first accommodating groove 21, or may be partially embedded in the inner circumferential surface of the first accommodating groove 21. Alternatively, the annular body may adopt other structures, for example, a ring body with a cooling channel inside. The ring body may be formed by butt-jointing a plurality of separate bodies, or may be of a one-piece structure, which is not particular limited by the embodiment of the present disclosure.

Third Embodiment

Figure 10:
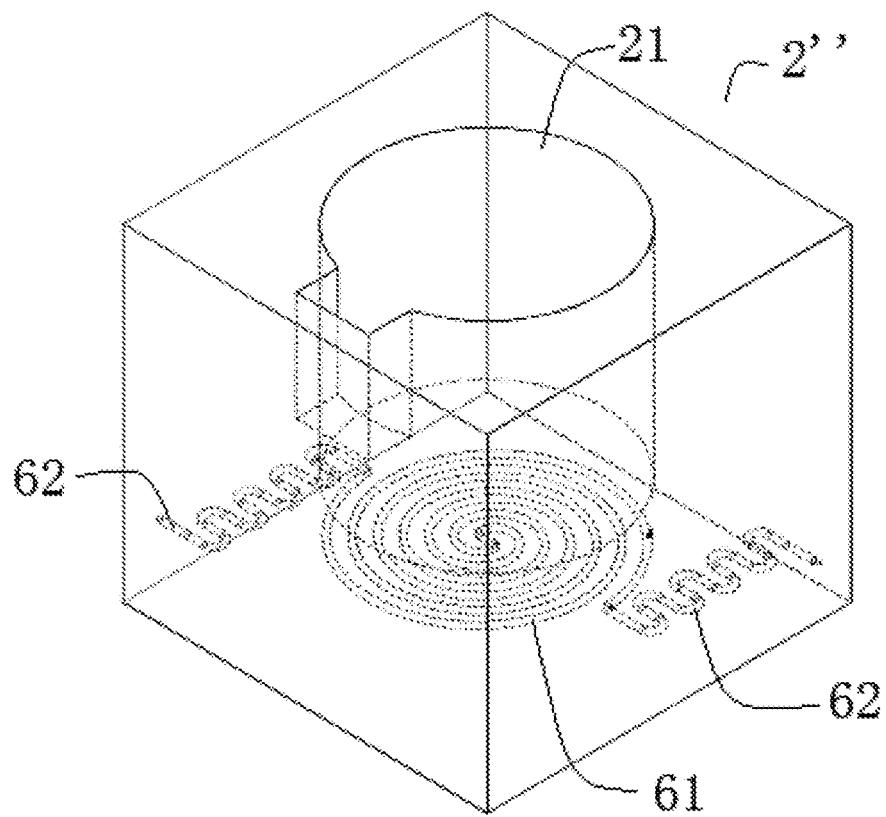
FIG. 10 is a perspective view of seeing through a heat dissipation structure in one of the first accommodating grooves adopted in a third embodiment of the present disclosure.
Figure 11:
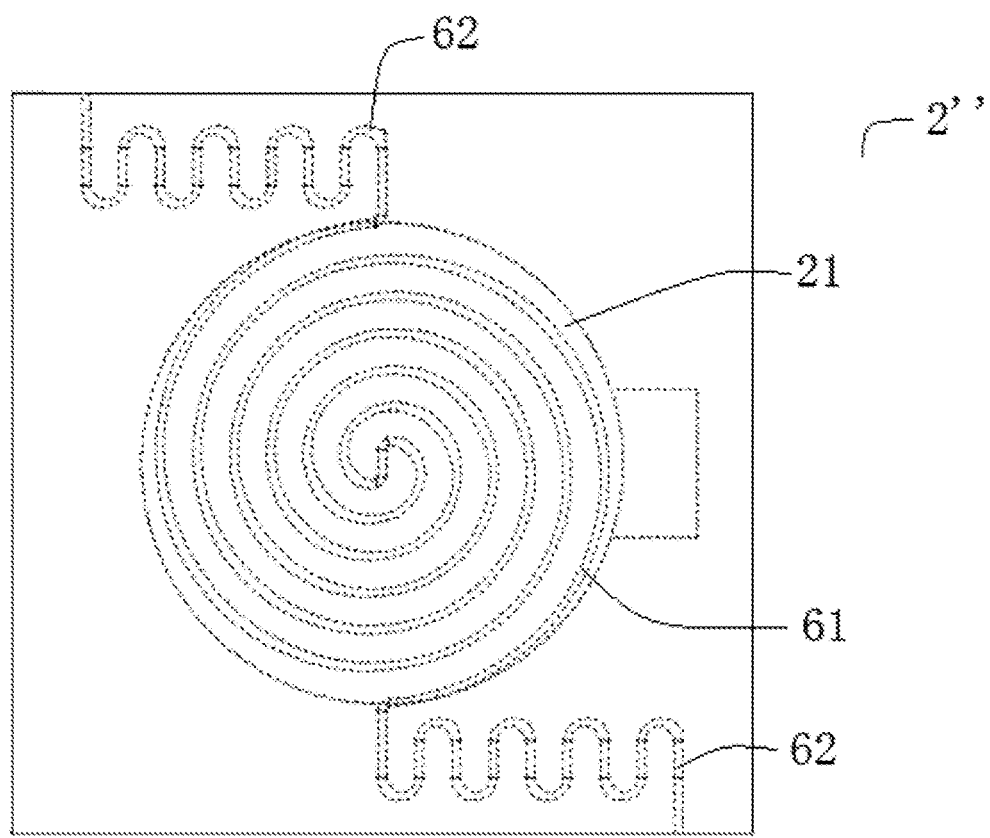
FIG. 11 is a top view of seeing through the heat dissipation structure in one of the first accommodating grooves adopted in the third embodiment of the present disclosure.

Compared with the first and second embodiments, a chip heat sink provided by the present embodiment has a different heat dissipation manner from those of the first and second embodiments. Specifically, as shown in FIGS. 10 and 11, in the present embodiment, the heat dissipation structure includes a cooling channel formed in the substrate 2" for conveying a cooling medium (e.g., cooling water). The cooling channel includes a cooling section 61 in a shape of a flat plate and two lead-out sections 62, where the cooling section 61 is located on a side of a bottom surface (parallel to the first surface 2a) of the first accommodating groove 21 away from the first surface 2a; the two lead-out sections 62 are connected to two ends of the cooling section 61, respectively, and the other end of each of the two lead-out sections 62 extends to an outer surface of the substrate 2"; an output end and an input end of a circulation pump (not shown in the drawings) are connected to the other ends of the two lead-out sections 62, respectively, for circulating the cooling medium in the cooling channel. The function of the circulation pump is the same as that of the second embodiment described above, and will not be repeated herein.

In some alternative embodiments, as shown in FIG. 11, the cooling sections 61 are wound in a planar spiral configuration. A plane, where the planar spiral structure is located, for example, is parallel to the bottom surface of the first accommodating groove 21, so as to uniformly dissipate heat. Specifically, for a circular electromagnet, the bottom surface of the first accommodating groove 21 is circular, and the planar spiral structure is correspondingly circular. Alternatively, the two lead-out sections 62 extend in a serpentine shape to lengthen the path, so as to improve the cooling efficiency of the substrate.

In summary, the chip heat sink provided by the above embodiments of the present disclosure can not only avoid the too high temperature of electromagnet affecting the effect of nucleic acid extraction and damaging the equipment and chip, but also indirectly control the temperature of the chip by controlling the temperature of the substrate through the heat dissipation structure, so as to enable the temperature of the chip to reach the operating temperature of an reaction such as loop-mediated isothermal amplification.

As another technical solution, an embodiment of the present disclosure further provides a nucleic acid extraction device, including a nucleic acid extraction microfluidic chip and the chip heat sink provided in each of the embodiments of the present disclosure, where the nucleic acid extraction microfluidic chip is placed on the first surface of the substrate in the chip heat sink.

According to the nucleic acid extraction device provided by the embodiment of the present disclosure, by adopting the chip heat sink provided by the embodiment of the present disclosure, it can not only avoid the too high temperature of electromagnet affecting the effect of nucleic acid extraction and damaging the equipment and chip, but also indirectly control the temperature of the chip by controlling the temperature of the substrate through the heat dissipation structure, so as to enable the temperature of the chip to reach the operating temperature of an reaction such as loop-mediated isothermal amplification, polymerase chain reaction, or the like.

It will be understood that the above embodiments are merely exemplary embodiments adopted to illustrate the principles of the present disclosure, and the present disclosure is not limited thereto. It will be apparent to one of ordinary skill in the art that various modifications and improvements can be made without departing from the spirit and scope of the present disclosure, and such modifications and improvements are also considered to be within the scope of the present disclosure.

What is claimed is:
1. A chip heat sink for a chip, wherein the chip has a channel for conveying a fluid, and on/off of the channel is controlled by a solenoid valve, and the chip heat sink comprises:

a substrate, wherein the substrate has a first surface for placing the chip, and the first surface is provided with a first accommodating groove for accommodating an electromagnet; and a heat dissipation structure on the substrate and for dissipating heat from the electromagnet.

2. The chip heat sink according to claim 1, wherein a shape of an orthographic projection of the first accommodating groove on the first surface is the same as a shape of an orthographic projection of the electromagnet on the first surface.

3. The chip heat sink according to claim 1, wherein a space exists between an outer surface of the electromagnet and an inner surface of the first accommodating groove opposite to the outer surface, and a thermally conductive material is filled in the space.

4. The chip heat sink according to claim 1, wherein a part of the electromagnet protrudes with respect to the first surface.

5. The chip heat sink according to claim 1, wherein the first surface is further provided with a lead recessed channel and a connecting groove connected between a first end of the lead recessed channel and the first accommodating groove, wherein the lead recessed channel is used for accommodating a power supply lead of the electromagnet, and a second end of the lead recessed channel extends to an edge of the substrate; and the connecting groove is used for accommodating a connecting part between the electromagnet and the power supply lead.

6. The chip heat sink according to claim 5, wherein a number of the first accommodating groove is one or more, and a number of the connecting groove is the same as the number of the first accommodating groove, and the one or more connecting grooves are connected to the one or more accommodating grooves in a one-to-one correspondence;

a number of the lead recessed channel is the same as the number of the first accommodating groove, and first ends of the lead recessed channels are connected to the connecting grooves in a one-to-one correspondence; second ends of the lead recessed channels independently extend to a same edge of the substrate; or the first surface is further provided with a main lead recessed channel, one of the main lead recessed channel extends to an edge of the substrate, at least one of the second ends of all the lead recessed channels is connected to the main lead recessed channel, and the second ends of the lead recessed channels not connected to the main lead recessed channel independently extend to the edge of the substrate where the one end of the main lead recessed channel is located; or the first surface is further provided with a branch lead recessed channel and a main lead recessed channel, one end of the main lead recessed channel extends to an edge of the substrate, the branch lead recessed channel comprises at least one branch lead recessed channel, a first end of each of the at least one branch lead recessed channel is connected to a second end of at least two of the lead recessed channels, and a second end of the branch lead recessed channel is connected to the main lead recessed channel; the second end of the lead recessed channel not connected to the branch lead recessed channel is connected to the main lead recessed channel or independently extends to the edge of the substrate where the one end of the main lead recessed channel is located.

7. The chip heat sink according to claim 1, wherein the chip further comprises at least one syringe, and the first surface is further provided with at least one second accommodating groove each for accommodating a part of one of the at least one syringe, and a number and a position of the at least one second accommodating groove is in one-to-one correspondence with a number and a position of the at least one syringe.

8. The chip heat sink according to claim 1, wherein the first surface is further provided with at least one positioning slot, and a number, a shape and a position of the at least one positioning slot are adapted to a number, a shape and a position of at least one designated protrusions on an outer surface of the chip, so that the at least one positioning slot is matched with the at least one designated protrusion to define a position of the chip on the first surface.

9. The chip heat sink according to claim 1, wherein two edge protrusions are further provided at two edges of the first surface on two opposite sides and protrude relative to the first surface, and surfaces of the two edge protrusions opposite to each other and the first surface form an accommodating space for defining the chip.

10. The chip heat sink according to claim 1, wherein the heat dissipation structure comprises:

a plurality of fins arranged at intervals on a second surface of the substrate away from the first surface; and a fan arranged on a side of the plurality of fins away from the substrate and for blowing air to the plurality of fins in a direction toward the second surface.

11. The chip heat sink according to claim 10, wherein the fan is attached and fixedly connected to the plurality of fins.

12. The chip heat sink according to claim 1, further comprising a support, wherein the support is on a side of the substrate away from the first surface, one end of the support is fixedly connected to the substrate, and the other end of the support is used to be fixedly connected to a nucleic acid extraction device where the chip is located.

13. The chip heat sink according to claim 1, wherein the heat dissipation structure comprises:

an annular cooling component around the electromagnet along an inner peripheral wall of the first accommodating groove, wherein the annular cooling component comprises an annular body having a cooling channel and a circulation pump communicated with two ends of the cooling channel, and the cooling channel is used for conveying a cooling medium; and the circulation pump is used for circulating the cooling medium in the cooling channel.

14. The chip heat sink according to claim 13, wherein the annular body comprises a cooling pipe wound in a cylindrical spiral configuration.

15. The chip heat sink according to claim 1, wherein the heat dissipation structure comprises:

a cooling channel formed in the substrate for conveying a cooling medium, wherein the cooling channel comprises a cooling section in a shape of a flat plate and two lead-out sections, wherein the cooling section is on a side of a bottom surface of the first accommodating groove away from the first surface; the two lead-out sections are connected to two ends of the cooling section, respectively, and the other end of each of the two lead-out sections extends to an outer surface of the substrate; and a circulation pump, wherein an output end and an input end of the circulation pump are connected to the other ends of the two lead-out sections, respectively, for circulating the cooling medium in the cooling channel.

16. The chip heat sink according to claim 15, wherein the cooling section is wound in a planar spiral configuration.

17. The chip heat sink according to claim 1, wherein the chip is a nucleic acid extraction microfluidic chip.

18. A nucleic acid extraction device comprising a nucleic acid extraction microfluidic chip and the chip heat sink according to claim 1, wherein the nucleic acid extraction microfluidic chip is on the first surface of the substrate in the chip heat sink.

19. The nucleic acid extraction device according to claim 18, wherein a shape of an orthographic projection of the first accommodating groove on the first surface is the same as a shape of an orthographic projection of the electromagnet on the first surface.

20. The nucleic acid extraction device according to claim 18, wherein a space exists between an outer surface of the electromagnet and an inner surface of the first accommodating groove opposite to the outer surface, and a thermally conductive material is filled in the space.

* * * * *